United States Patent
Wilson

(10) Patent No.: US 7,214,190 B1
(45) Date of Patent: May 8, 2007

(54) APPARATUS AND METHOD FOR NONINVASIVE MONITORING OF ANALYTES IN BODY FLUIDS

(76) Inventor: Kitchener Clark Wilson, 415 Calle Las Caleras, Santa Barbara, CA (US) 93109

( * ) Notice: Subject to any disclaimer, the term of this patent is extended or adjusted under 35 U.S.C. 154(b) by 343 days.

(21) Appl. No.: 10/936,851

(22) Filed: Sep. 9, 2004

Related U.S. Application Data

(60) Provisional application No. 60/545,017, filed on Feb. 17, 2004, provisional application No. 60/501,446, filed on Sep. 9, 2003.

(51) Int. Cl.
*A61B 5/00* (2006.01)
(52) U.S. Cl. .................. 600/309; 600/310
(58) Field of Classification Search ........ 600/309, 600/310, 312, 317, 329
See application file for complete search history.

(56) References Cited

U.S. PATENT DOCUMENTS

| | | | |
|---|---|---|---|
| 4,344,438 A | | 8/1982 | Schultz |
| 5,127,405 A | * | 7/1992 | Alcala et al. ............ 600/342 |
| 5,250,285 A | * | 10/1993 | Lauffer et al. .......... 424/9.361 |
| 5,569,186 A | * | 10/1996 | Lord et al. .................. 604/67 |
| 5,612,034 A | | 3/1997 | Pouletty et al. |
| 5,843,440 A | | 12/1998 | Pouletty et al. |
| 6,103,233 A | | 8/2000 | Pouletty et al. |
| 6,123,134 A | | 9/2000 | Stark |
| 6,181,957 B1 | | 1/2001 | Lambert et al. |
| 6,197,534 B1 | * | 3/2001 | Lakowicz et al. ........... 435/14 |
| 6,197,928 B1 | | 3/2001 | Tsien et al. |
| 6,236,047 B1 | | 5/2001 | Malin et al. |
| 6,593,295 B2 | | 7/2003 | Bridon et al. |
| 6,675,030 B2 | | 1/2004 | Ciurczak et al. |
| 6,681,127 B2 | | 1/2004 | March |

* cited by examiner

*Primary Examiner*—Eric Winakur
*Assistant Examiner*—Etsub Berhanu
(74) *Attorney, Agent, or Firm*—Richard S. Erbe

(57) ABSTRACT

Noninvasive in vivo real time analyte measurement uses a multitude of sensors binding reversibly to the analyte whereby the response of the sensors to a noninvasive stimulus is altered by their bound versus unbound state. The stimulus and responses are electromagnetic, magnetic or any other suitable forms. The sensors are bound to a blood component providing transport through the body fluids and sensor elimination. A sensor is constructed from proteins or as a nanodevice. A noninvasive device generates the stimulus, senses the responses, determines the measurement, and controls a medication infusion pump. A non-contact device is used for population screening, and one form of such a device is a nuclear magnetic resonance imager. Measurement in fluids other than blood uses a blood component flowing out of blood and into the desired fluid.

14 Claims, 12 Drawing Sheets

APPARATUS AND METHOD FOR NONINVASIVE MONITORING OF ANALYTES IN BODY FLUIDS

RELATED APPLICATIONS

This application claims the benefit of U.S. Provisional Application Ser. Nos. 60/501,446, filed 9 Sep., 2003 and 60/545,017 filed 17, Feb. 2004, all of which are incorporated herein by reference in their entireties.

BACKGROUND OF THE INVENTION

1. Field of the Invention

The present invention relates generally to devices and methods for monitoring of analytes that may be found in body fluids, and more particularly to an apparatus and method for continuous noninvasive monitoring and measurement of analytes found in vascular and extravascular body fluid pools including interstitial, lymph and cerebral spinal fluids.

2. General Background and State of the Art

It is desirable to have a method for measuring or monitoring the levels of analytes present in the body fluids in a noninvasive manner. By noninvasive is meant a manner that does not require breaking the skin of the subject to obtain a measurement. Breaking the skin, or otherwise invading the body of the subject, can require a skilled medical technician to perform the procedure in order not to introduce bacteria or other complications. A noninvasive manner that does not require a technician, cannot introduce bacteria, and that can be performed simply by the subject is much preferred.

It is furthermore desirable to provide a device and method to continuously, or nearly continuously, monitor the levels of the analyte. Intermittent body fluid sampling may not detect transient changes in the analyte while continuous monitoring can.

Examples of desirable analyte measurements for such a device and method include:
- blood: glucose
- blood: hormones
- blood: therapeutic drugs
- blood: cocaine
- blood: HIV antibodies
- interstitial and lymph fluid: cancer precursors
- cerebral spinal fluid: Alzheimer precursors
- blood: creatinine to monitor kidney function for dialysis
- blood: bilirubin, AST, ALD, alkaline phosphatase to monitor liver function in cirrhosis Given that diabetes is predicted to become an international epidemic due to changes in the eating habits of the world population and increasingly sedentary lifestyles, noninvasive glucose measurement is of particular interest. Most of the long term affects of diabetes are due to untreated hyperglycemia and currently there is not an effective noninvasive continuous glucose measurement method available. Diabetics are left to painfully sample their blood many times each day in order to determine glucose concentration and adjust their insulin dosage accordingly. The present invention provides a method and apparatus for continuous noninvasive blood glucose monitoring.

Given the critical nature of glucose monitoring, there are a number of known devices in the field for noninvasive optical scanning of a body part followed by data analysis to infer glucose concentration. For example, U.S. Pat. No. 6,675,030 to Ciurczak, et al. discloses a multi-spectral scanner to view a body part and infer the glucose concentration using a mathematical model correlated to the subject using invasive samples.

U.S. Pat. No. 6,236,047 to Malin, et al. discloses a method that illuminates the body part with various optical energies and determines analyte concentration by analyzing the reflected radiation.

U.S. Pat. No. 6,181,957 to Lambert, et al. discloses a method using an optical beam imaged on the eye and determines glucose concentration by analyzing the reflected radiation.

U.S. Pat. No. 6,124,134 to Stark discloses a device that irradiates the body with electromagnetic radiation and determines glucose concentration by analyzing the resulting spectrum.

The basis of the Ciurczak, et al., Malin, Lambert, et al., and Stark inventions is the assumption that the analyte to be measured, or its normal blood compounds, substantially influence the reflected or transmitted portion of electromagnetic radiation.

U.S. Pat. No. 6,681,127 to March discloses a contact lens having a binding site for the analyte and an analyte competitor for the same site. The competitor is fluorescent when in the unbound state.

U.S. Pat. No. 4,344,438 to Schultz discloses a method that includes inserting a capsule having receptors into the blood stream. The concentration of the analyte is determined by the fluorescence of a competitor for the same site.

U.S. Pat. No. 6,197,928 to Tsien, et al. discloses a fluorescent binding protein manufactured within a cell by modifying its DNA sequence to detect analytes.

The basis of the March, Schultz, and Tsien inventions is the provision of a binding site that changes its measurable optical characteristics when bound to the desired analyte.

SUMMARY OF THE INVENTION

Accordingly, it is an object of the present invention to provide a noninvasive nearly continuous method and device to measure a selected analyte within the body fluid compartments including vascular, interstitial, lymph, cerebral spinal, etc.

It is yet another object of the invention to provide a method and device for nearly continuous noninvasive monitoring of analytes that does not require cellular DNA sequence modification, ocular lenses, nor a capsule within the blood stream.

It is yet another object of the invention to provide a method and device for nearly continuous noninvasive monitoring of analytes that does not require the analytes to respond to a stimulus.

It is yet another object of the invention to provide a method and device for nearly continuous noninvasive monitoring of analytes for mass population screening that does not require medical personnel.

These and other objectives are achieved by the present invention, which, in a broad aspect, provides specifically designed sensors that respond both to a specific analyte and to an external stimulus.

A device and method according to the preferred embodiment of the invention provides a plurality of sensors for administration into the fluid compartments of the subject. Each sensor is designed to bind reversibly and selectively to the analyte to be measured and undergo a physical or chemical change such that the sensor response to a stimulus is altered when bound to the analyte from when it is not bound.

Each sensor is made up of three main components: 1) a reversible binding site for analyte binding; 2) a signaling site; and 3) a transporter-eliminator binding site. The signaling site responds to the bound/unbound status of the binding site and sends a status signal in response to an external stimulus. The transporter-eliminator binding site binds to a blood component to provide sensor transportation through the vascular or extravascular compartments and to also provide an elimination pathway. If the component has a known body elimination rate or half-life, the sensors are eliminated at the same rate.

Many blood components, like albumin, leave the vascular space and travel through the extravascular body fluid compartments and, carrying the sensor, make it possible to perform measurements of analytes that are primarily outside of the blood and in the other fluid compartments such as interstitial, lymph and cerebral spinal fluids. Since albumin does not cross the blood-brain barrier, a smaller transport-eliminator is needed for the cerebral spinal fluid. If an adequate endogenous transporter-eliminator is not found, an engineered one is administered with the sensor.

The sensor of the present invention is designed to respond to various stimuli including electromagnetic, magnetic, or other suitable forms. The analyte binding status signal sent by each sensor in response to the stimulus is measured remotely and noninvasively and related to the analyte measurement. Once the analyte measurement is determined, an infusion pump provides medication.

One version of the sensor responds with a signal only when bound (or unbound), and no signal distinguishable from background otherwise. The known binding characteristics of the analyte binding site, the known elimination rate of the sensor, and subject calibration parameters are used to relate the response to the analyte measurement.

A second version of the sensor responds with distinct signals when bound and unbound, both different from background. The analyte measurement is determined from these signals and the known binding characteristics alone, without requiring a known elimination rate nor subject calibration.

Further objects and advantages of the present invention will become more apparent from the following description of the preferred embodiments, which, taken in conjunction with the accompanying drawings, will illustrate, by way of example, the principles of the invention.

BRIEF DESCRIPTION OF THE DRAWINGS

The foregoing and other objects, aspects and advantages will be better understood from the following detailed description of the preferred embodiments of the invention with reference to the drawings in which.

DETAILED DESCRIPTION OF THE PREFERRED EMBODIMENTS OF THE INVENTION

Figure 1:
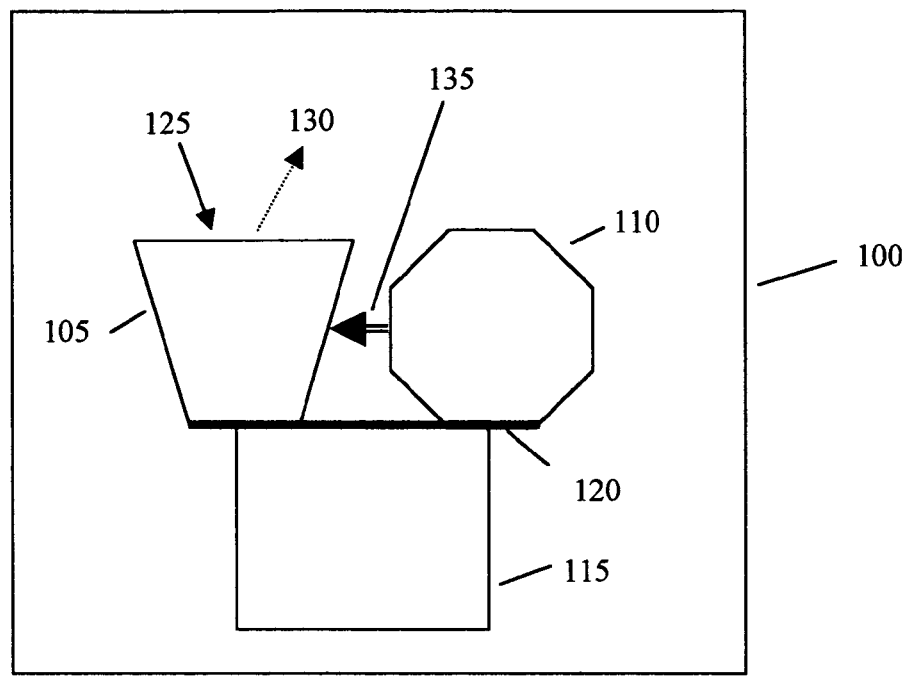
FIG. 1 illustrates a schematic of an exemplary sensor structure according to the present invention showing the analyte binding site, signaling site, influence of the binding site status on the signaling site, transporter-eliminator binding site, and substrate.

In the following description of the present invention, reference is made to the accompanying drawings, which form a part thereof, and in which are shown, by way of illustration, exemplary embodiments illustrating the principles of the present invention and how it may be practiced. It is to be understood that other embodiments may be utilized to practice the present invention and structural and functional changes may be made thereto without departing from the scope of the present invention.

Overview: Many analytes of interest do not respond adequately to stimuli (e.g. electromagnetic, magnetic), and it is more effective to provide a specifically designed (e.g. an engineered protein or nanodevice) sensor that responds both to the analyte and to a stimulus. Such a sensor is under the control of the designer and is tailored as needed.

The stimulus is an energy source flooding the region where the analyte is to be measured and powering the sensor response. Stimuli include light and other electromagnetic signals, and magnetic fields. The sensor measurable response includes fluorescence; stimulus absorption, reflection and transmittance; and radio frequency emission.

A noninvasive stimulator-detector device is used to stimulate a portion of the body containing the analyte and sensor and to detect the cumulative response of the stimulated sensors. The stimulator-detector determines the analyte measurement intermittently or in a continuous or near-continuous fashion. This information is provided to the subject on a display that alerts him should the analyte be outside an acceptable range. The noninvasive stimulator-detector is also used to control the infusion of a medication (e.g. insulin in the case of glucose and diabetes) by activating a medication pump based on the analyte measurement.

The designed sensor is made to reversibly bind to the analyte and, in so doing, undergo a conformational or chemical or other change such that its response to the stimulus is altered from its response in the unbound state. By stimulating the sensor and detecting this alteration, the bound status of the sensor is determined. Because more than one sensor is introduced, the cumulative status of the ensemble of sensors is determined and related to the analyte measurement through the known analyte-sensor binding characteristics.

It is desirable for the sensor to reside in that portion of the blood vessels where the majority of the blood flows. This is accomplished by transporting the sensor attached to a blood component like albumin or other endogenous blood protein, red blood cell, platelet, etc.

It is also desirable for the sensor to be capable of entering body pools other than blood. This is accomplished by transporting the sensor attached to a blood component, like albumin, which leaves blood through the capillaries and returns having passed through the extravascular body pools.

Sensor elimination is important to clear it from the subject should he have an unexpected allergic or immune response to the sensor. It is also important in order to adjust the amount of sensor within the subject and to clear the sensor from blood at a known rate. This is again accomplished by binding the sensor to a blood component having a known and desired decay rate. Suitable candidates are albumin (15–19 day half-life), platelets (7–10 days), red blood cells (120 days), and other blood components.

Albumin is a large protein synthesized in the liver and released into blood with 40–45% present intravascular and 55–60% in extravascular space. Intravascular albumin maintains the osmotic pressure of blood, and passes through the capillary endothelium into the extravascular space. The flow of vascular to extravascular albumin is 4–5%/hr (100% turnover in 1 day) and returning through the lymph system. With its four active binding sites, albumin is a transporter of substances that are otherwise quickly degraded (e.g. thyroid hormones, insulin, steroid hormones, bilirubin), of drugs (e.g. warfarin, salicylate, clofibrate, phenylbutazone), and of other metabolites (e.g. calcium, long chain fatty acids).

The kidney behaves as though it has 100 Å diameter pores; albumin acts like it has a clearance radius of 35.3 Å, yet is only slightly passed by glomerular filtration into the kidney tubules where it is engulfed and absorbed (pinocytosis) by the tubule cells. Intra-cellular enzymes (lysosome proteases) break up the albumin molecule with its amino acid elements returned to blood. Albumin is cleared in a similar manner by the intestinal lumen cells. The sensor is designed to follow these elimination pathways by riding piggyback on albumin and is thus engulfed by the kidney tubule and intestinal lumen cells and there attacked by enzymic processes that render the sensor inoperable and available for elimination from the body, or its components recycled by normal metabolism.

If the endogenous blood components are not adequate, a physiologically compatible substance is administered along with the sensor to provide the transport-elimination function. The elimination of the sensor will follow that of the provided substance.

Half of the introduced sensors are lost every half-life of the transporter-eliminator to which it is bound and, after one or more of these intervals, the signal-to-noise of the remaining sensors will be reduced to the point where more sensors must be administered to continue monitoring.

Administration of the sensors is by intra-muscular, sub-cutaneous or intra-venous injection, or by inhalation or ingestion or any other satisfactory means. If the administration of the sensor is by injection, at least this invasive process is reduced to once every few half-lives of the transporter-eliminator.

Multiple sensor types with affinities to different analytes are mixed if their signaling sites generate non-conflicting signals, or if the signaling sites respond to distinct stimuli.

Stimulus: The external stimulus is a key element of this device. One version of this stimulus is selected from the portion of the electromagnetic spectrum between the infrared to high ultraviolet. Infrared signals cause molecular vibration (also known as heat) and are absorbed. Visible light has stronger absorption by causing electron transitions to higher energy states and some molecules fluoresce when the electrons fall back by emitting a photon of light at very specific wavelengths. Fluorescence is the basis of many routine measurements. Ultraviolet light is very strongly absorbed by causing electron energy transitions and is fully absorbed by the skin, the largest organ of the body. Signals at and above high frequency ultraviolet should be avoided as they can strip away electrons and ionize molecules.

Consider the electromagnetic spectrum from low frequency radio signals up to infrared. Radio signals have too long a wavelength to directly affect very small structures. Microwave and millimeter wave signals are to a small extent absorbed by causing molecular rotation (heat). In general, these signals are poorly absorbed and are not useful, but this changes when the sample is exposed to a magnetic field as in nuclear magnetic resonance (NMR) imaging or spectroscopy. The equipment for NMR spectroscopy is not nearly as large and complex as that of the more familiar NMR imaging used for diagnosis because imaging is not required, only chemical detection.

Atoms with nuclear spin (having unpaired electrons, protons, or neutrons) are aligned by a static magnetic field and can respond to a radio frequency signal with a different and detectable radio frequency emission. When the radio frequency signal is in resonance with the nuclear spins, the spins are perturbed from equilibrium and both the resonant frequency ("chemical shift") of the spins and the time to return to equilibrium (relaxation time constant) are fundamental NMR measurements. The chemical shift depends on the local electronic environment of the nucleus and is sensitive to the molecular structure. The relaxation time constant depends on dynamic fluctuations in the molecule. NMR measures connectivities and proximities of nuclei within a molecule through spin—spin coupling constants such as J-couplings (through-bond) and dipolar couplings (through-space). Almost every element of the periodic table has an isotope with spin; commonly used elements are $^1H$, $^2H$, $^{31}P$, $^{23}Na$, $^{14}N$, $^{13}C$, and $^{19F}$. When close together, the spins of these isotopes influence each other (spin—spin coupling) in a manner that is detectably different from when they are further apart and do not interact, and this interaction is commonly used to investigate chemical structure. Magnetic fields and radio frequency stimuli are not blocked by the skin and can penetrate deeper into the body than can stimuli from the electromagnetic spectrum between the infrared to high ultraviolet.

Binding between two molecules is both a chemical and a mechanical phenomenon where electrons are shared (chemical) and the new union produces a spatial shape change (mechanical conformation) in one or both molecules as they adjust to the bound status. The conformation moves apart portions (branches) of the molecules that may have been nearby prior the union, and brings others together. In this way the local chemistry of the branches is changed, causing the molecule to respond differently to stimuli.

Figure 2:
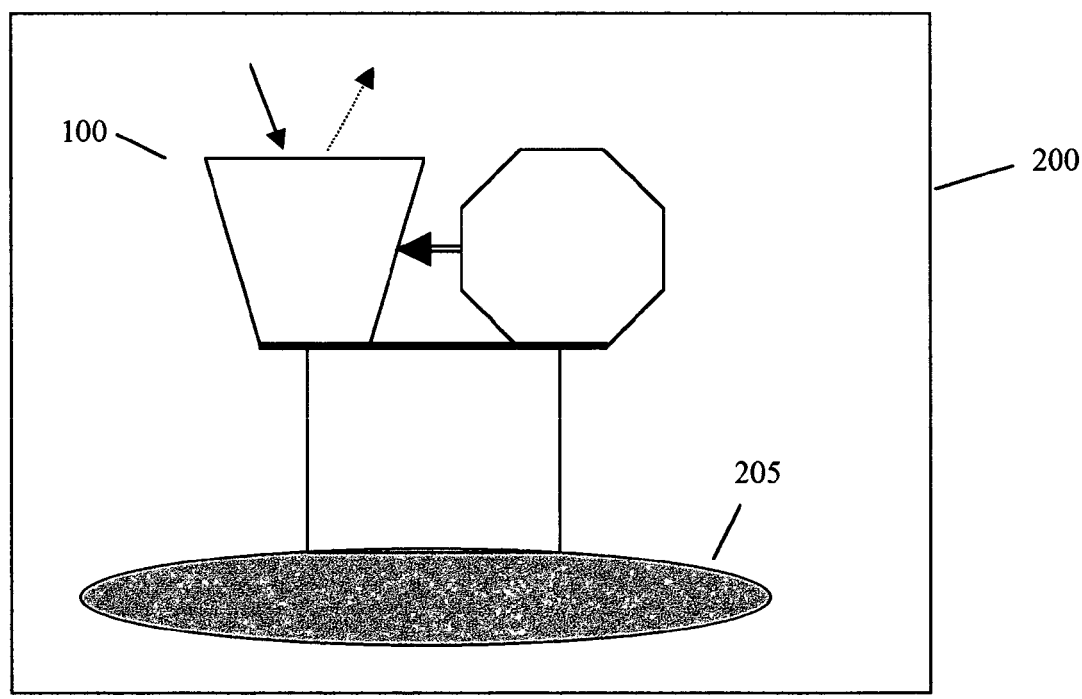
FIG. 2 illustrates a schematic of an exemplary sensor structure according to the present invention showing the sensor bound to the transporter-eliminator.
Figure 3:
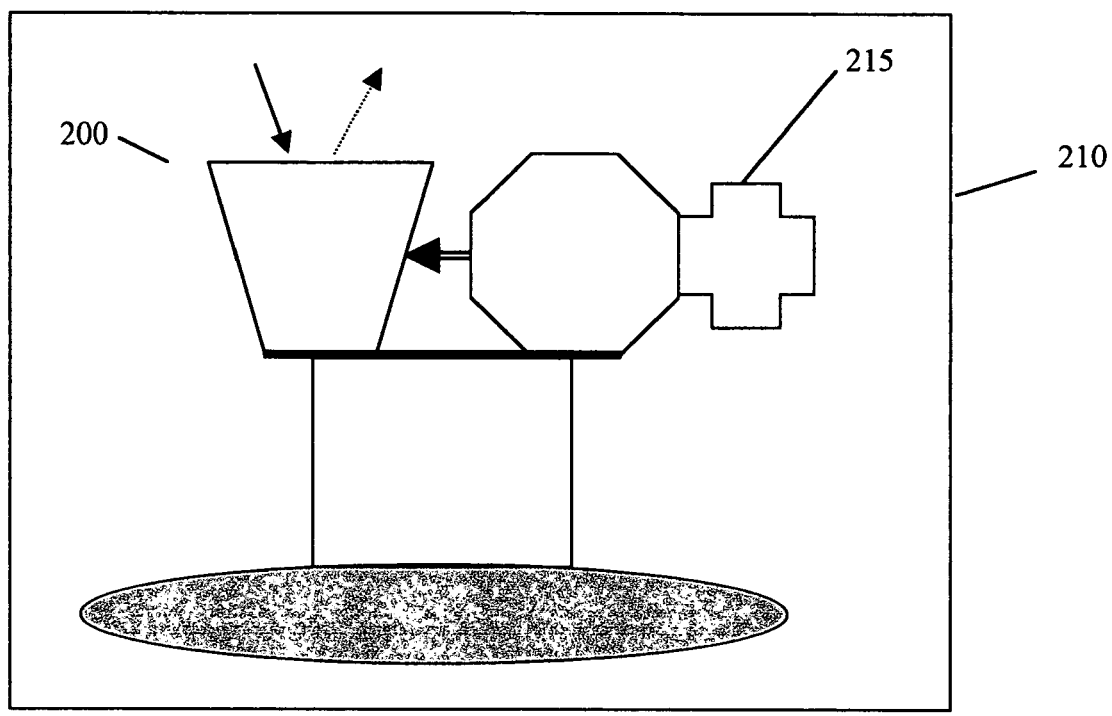
FIG. 3 illustrates a schematic of an exemplary sensor structure according to the present invention showing the sensor bound to the transporter-eliminator and to the analyte.

Sensor structure: FIG. 1 illustrates the sensor, which is designated by the reference numeral 100. Sensor 100 consists of three major components: a reversible analyte binding site 110, transporter-eliminator binding site 115, and a signaling site 105. The analyte binding site 110 is reversible in the chemical sense that the binding dynamics allow association of the analyte 215 to the binding site 110, as illustrated in FIG. 3, as well as dissociation depending on the concentrations of the two such that a measure of the bound analyte 215 reflects the total analyte. The transporter-eliminator binding is strongly associative, preferably covalent, to strongly bind the sensor 100 to the transporter-eliminator 205, as illustrated in FIG. 2, so that once bound they remain so. The bound/unbound status of the analyte binding site 110 is arranged to influence the signaling site 105 such that the signaling site 105 is responsive both to the status of the analyte binding site 110 and to the remote stimulus 125. The signaling site 105 responds 130 to the stimulus 125 and influence 135 to indicate the status of the analyte binding site 110. A fourth component of sensor 100 is substrate 120 on which the three major components are arranged.

The sensor-transporter-eliminator conjugate 200 structure is illustrated in FIG. 2, which shows sensor 100 bound to transporter-eliminator 205. The sensor-transporter-eliminator-analyte conjugate 210 structure is illustrated in FIG. 3, showing analyte 215 bound to sensor-transporter-eliminator conjugate 200. Techniques for creating analyte binding proteins are well established, as are techniques for creating transporter-eliminator binding proteins and for modifying a binding protein to generate a measurable response.

Figure 4:
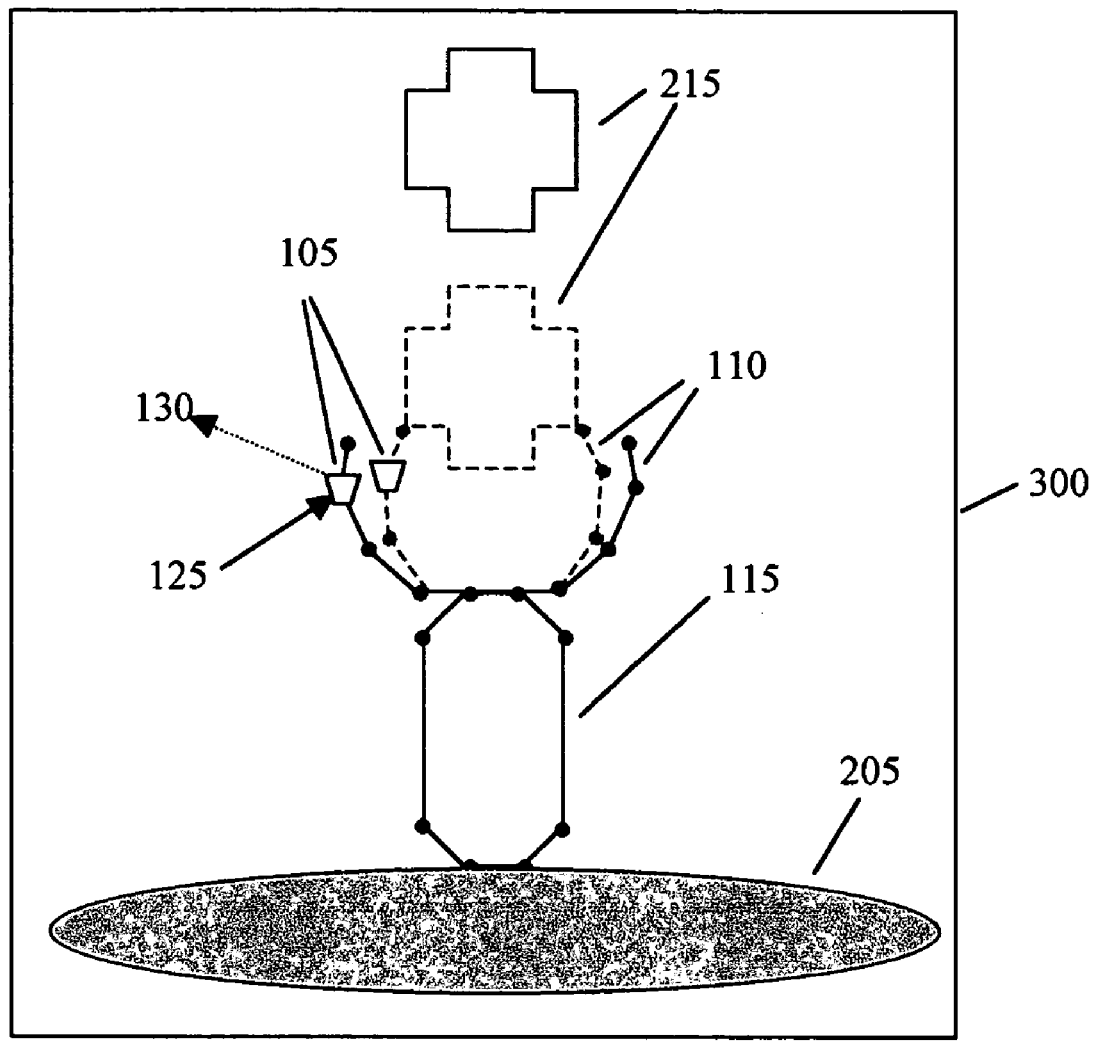
FIG. 4 illustrates a schematic of an exemplary sensor structure according to the present invention using protein based construction showing the unbound state (solid lines) and the bound state (dotted lines)

A protein-based form 300 of the sensor 100 has, for example and as illustrated in FIG. 4, an analyte binding site 110 protein modified to include the signaling site 105. The signaling site 105 is, for example, fluorescent and responds 130 with fluorescence when exposed to infrared through ultraviolet optical stimulus 125 when the analyte binding site 110 is bound to the analyte 215, but not when unbound, or alters its absorption or reflection of the stimulus 125. In another form, the signaling site 105 contain molecular nuclei with spin that respond to radio frequency and magnetic field stimuli 125 differently when analyte 215 is bound than when unbound. A protein transporter-eliminator binding site 115 is included to connect the analyte binding site 110 to the transporter-eliminator 205.

As an example, consider glucose analyte 215 measurement with albumin as the transporter-eliminator 205. The analyte binding site 215 is a protein engineered from glucose/galactose binding protein (GGBP) of *Escherichia coli* with its binding dissociation constant adjusted as needed. A fluorescent molecule signaling site 105 is added within the GGBP protein matrix at a location providing the desired response 130 and responding to the influence 135 of the conformational change upon analyte binding. The resulting analyte binding site 110 and signaling site 105 complex is conjugated to a transporter-eliminator 205 engineered from albumin binding DG12 protein (ABP) from Group G Streptococci.

Figure 5:
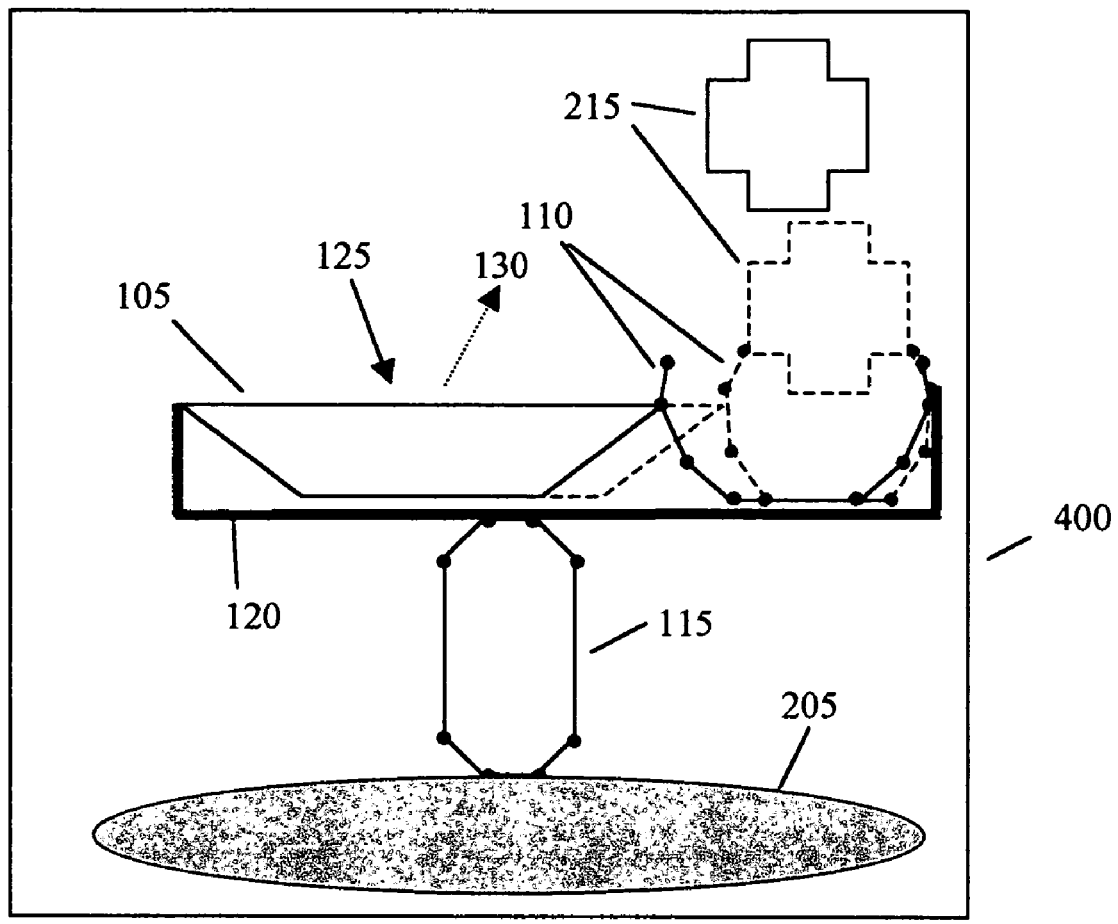
FIG. 5 illustrates a schematic of an exemplary sensor structure according to the present invention showing a nanodevice based construction with the unbound state (solid lines) and the bound state (dotted lines)

As shown in FIG. 5, another form of the sensor 100 is constructed as a nanodevice 400 having a substrate 120. The typically silicon substrate 120 forms a base to which the analyte binding site 110 (e.g. GGBP), the signaling site 105, and the transporter-eliminator binding site 115 (e.g. ABP) are conjugated. The analyte binding site 110 is arranged such that the change in its bound-to-analyte and unbound-to-analyte status is coupled to the signaling site 105 so as to influence and alter the stimulus response 130 of the signaling site 105. As an example, the signaling site 105 is one or more linked interacting nanoparticles, or quantum dots, and the conformational change stretches or compresses the signaling site 105, altering its response 130 to the stimulus 125. The signaling site 105 nanoparticle(s), for example, are constructed to be fluorescent when exposed to infrared to ultraviolet optical stimulus 125 when the analyte binding site 110 is bound to the analyte 215 but not when unbound, or the absorption or reflection of the stimulus 125 is altered. In another form of sensor 100, the signaling site 105 nanoparticle(s) contains molecular nuclei with spin that respond to radio frequency and magnetic fields differently when analyte 215 is bound than when unbound.

Figure 6:
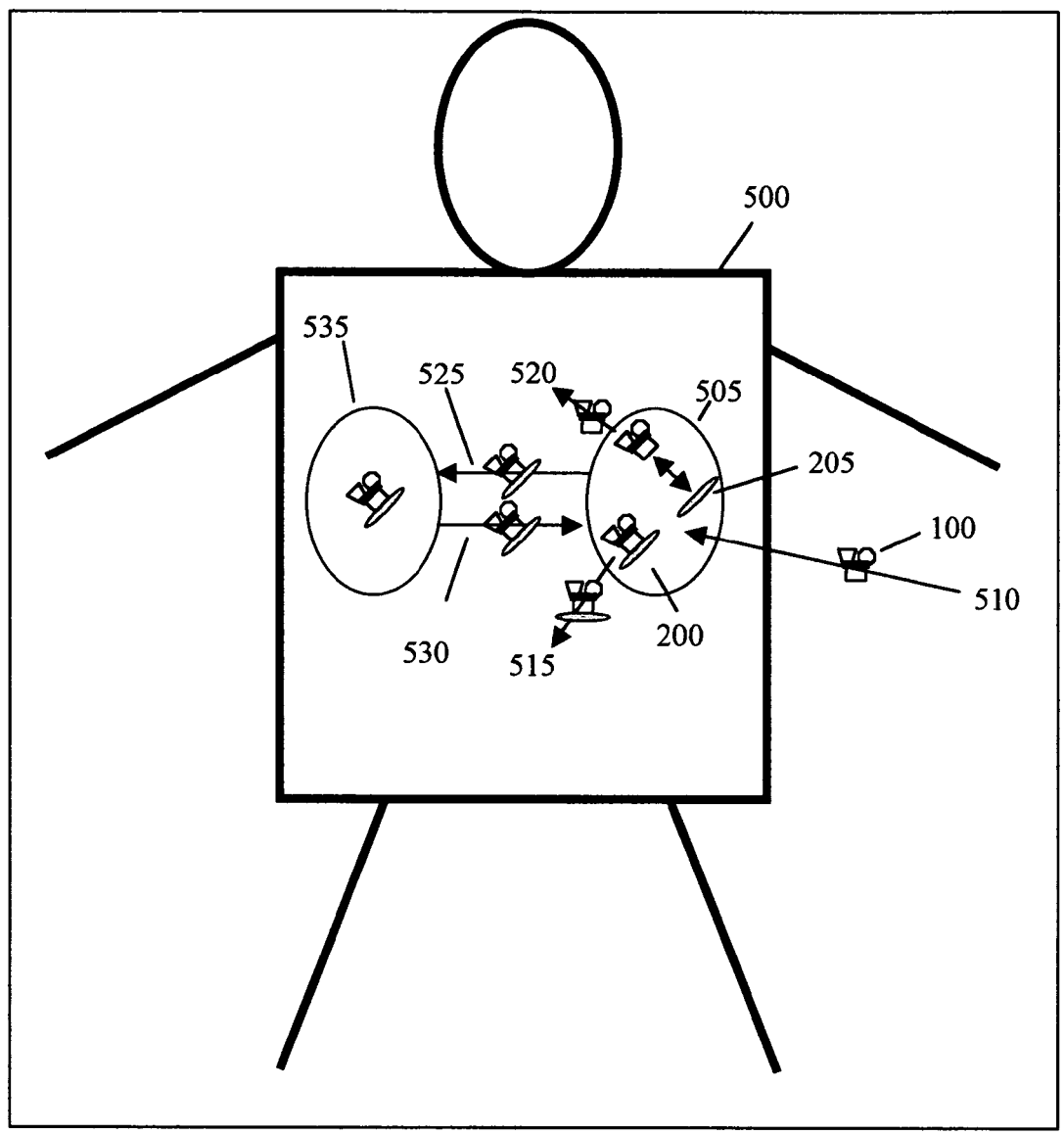
FIG. 6 illustrates a schematic of the metabolism of the sensor showing its administration into the blood pool, binding to a blood component, flow into and return from the extravascular body fluids, elimination from blood following the elimination of the blood component, and elimination when not bound to a blood component.

As illustrated in FIG. 6, the metabolism of the sensor 100 consists of administration pathway 510 into the subject 500 blood pool 505, formation of transporter-eliminator-sensor conjugates 200, flow 525 out of the blood pool 505 into the extravascular fluid pools 535, flow 530 from the extravascular fluid pools 535 to the blood pool 505, transporter-eliminator 205 mediated elimination pathway 515 from the blood pool 505, and elimination 520 of sensors 100 that have not formed transporter-eliminator conjugates. Administration pathway 510 is intra-muscular, subcutaneous, intravenous injection, inhalation, ingestion, or any other satisfactory means. Transporter-eliminator 205 mediated elimination pathway 515 parallels the normal transporter-eliminator 205 degradation mechanisms. Elimination pathway 520 is not mediated by the transporter-eliminator 205, and is any of many means the body has of clearing blood (e.g. kidney excretion, cellular pinocytosis, enzyme degradation). Sensor 100 is designed such that this non-mediated elimination pathway 520 is faster than the mediated pathway 515 to eliminate un-conjugated sensor 100.

Figure 7:
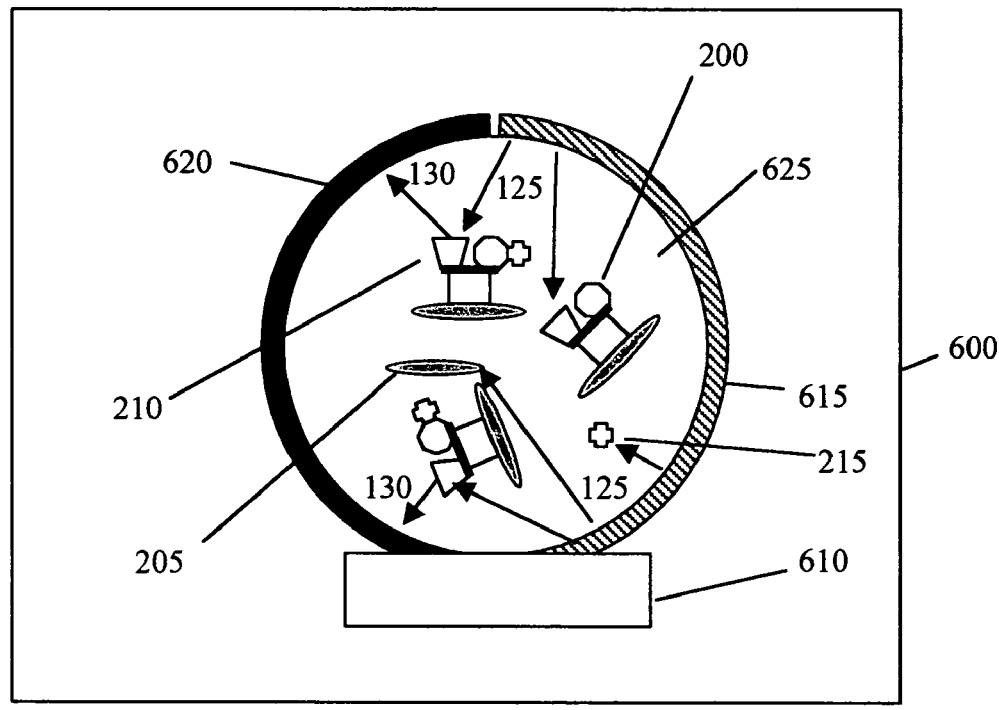
FIG. 7 illustrates a schematic of an exemplary stimulator-detector device according to the present invention and its interaction with sensors in the subject body fluids.

Noninvasive stimulator-detector device: As illustrated in FIG. 7, the stimulator-detector device 600 consists of a processor-display 610, at least one stimulator 615 (electromagnetic, magnetic, etc.) to generate the stimulus 125, at least one detector 620 to sense the response 130 of the sensors 100 to the stimulus 125, and may surround the portion 625 of the body to be monitored. As shown, the transporter-eliminator-sensor-analyte conjugates 210 respond 130 differently to the stimuli 125 than do the free transporter-eliminator 205, the transporter-eliminator-sensor conjugates 200 without bound analyte 215, or the unbound analyte 215.

Figure 8:
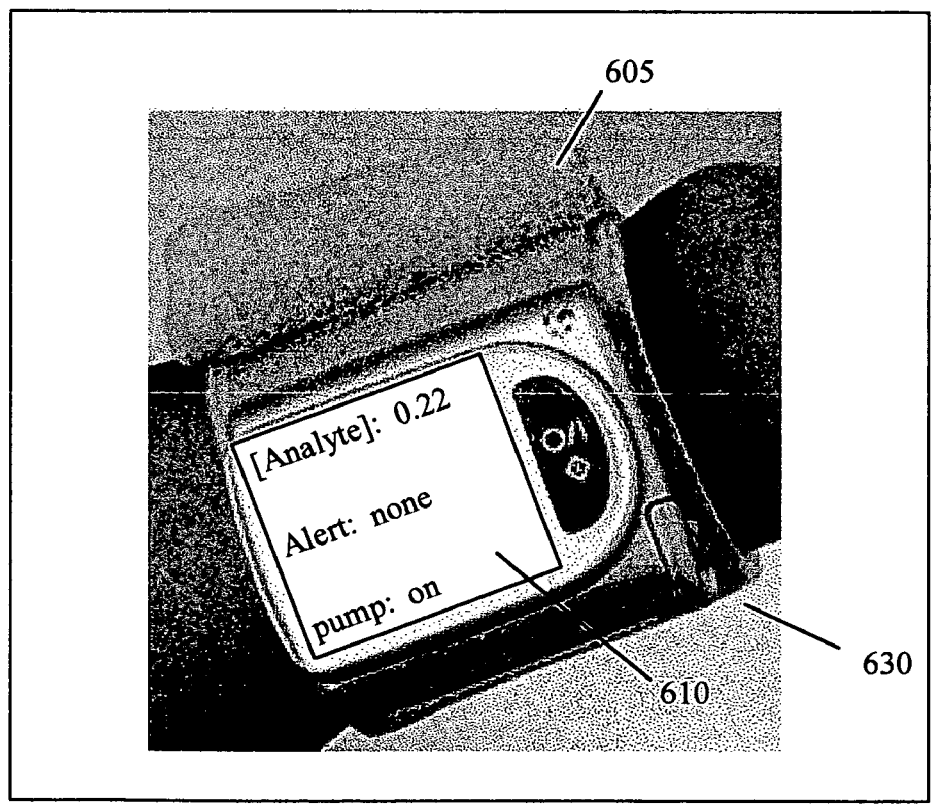
FIG. 8 illustrates a schematic of an exemplary personal stimulator-detector according to the present invention.

As illustrated in FIG. 8, a personal version 630 of the stimulator-detector device 600 is portable and positioned on the portion 625 of the body to be monitored using a cuff or strap 605. The analyte measurement is read from processor-display 610, and the preferred stimulus 125 for this battery operated portable device is visible to ultraviolet radiation stimulating a fluorescent sensor response 130 monitored by optical detectors 620.

Figure 9:
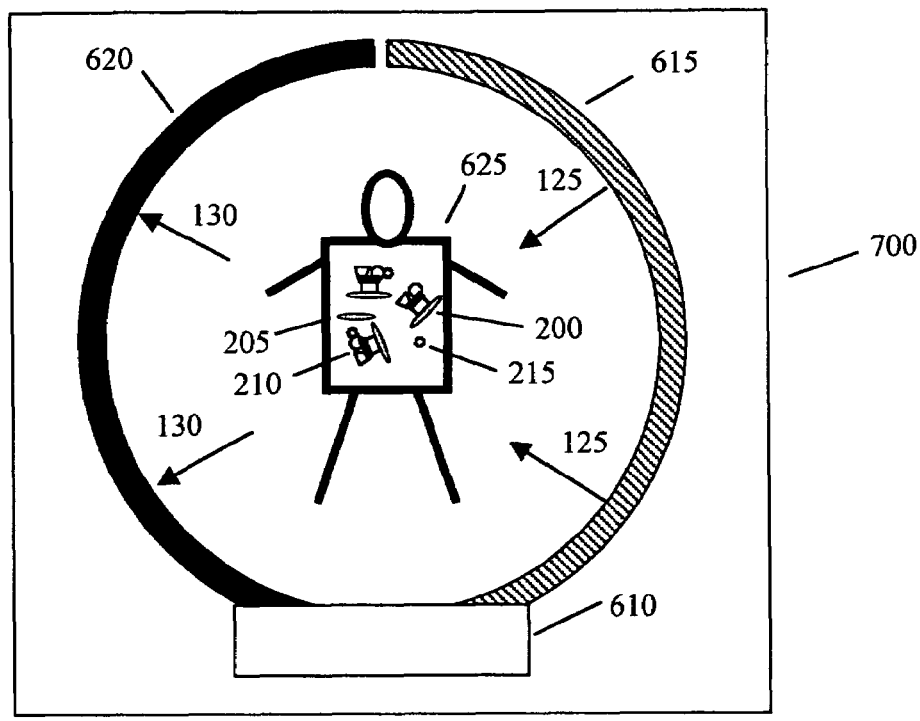
FIG. 9 illustrates a schematic of an exemplary remote stimulator-detector in accordance with the present invention.

As illustrated in FIG. 9, an alternate version 700 of the noninvasive stimulator-detector device 600 does not make direct contact with the subject but stimulates 125 and detects 620 the signaling site 105 response 130 at a distance. This remote stimulator-detector 700 is used to screen subjects with whole body or extremity monitoring much as metal detectors now do at airports and schools. The preferred stimulus 125 is a radio frequency field stimulating a radio frequency sensor response 130 monitored by a radio frequency detector 620, under the influence of a magnetic field stimulus 125 that activates the nuclear magnetic resonance phenomenon.

The imaging NMR systems commonly used in hospital settings are forms of the non-contacting stimulator-detector device 700 with which the analyte 215 measurement and the locations in the body of the actively reporting sensors 210 are determined. The location information provides powerful diagnostic information.

Figure 10:
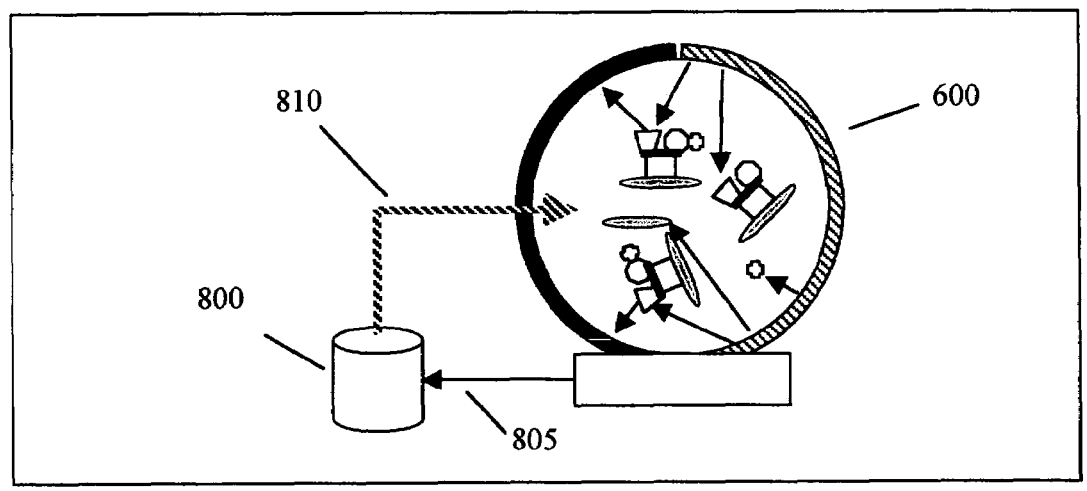
FIG. 10 illustrates a schematic of an exemplary stimulator-detector controlling a medication pump.

Medication infusion pump control: A medication infusion pump 800 is connected to the stimulator-detector device 600 to apply medication 810 in response to the analyte 215 measurement as illustrated in FIG. 10. The pump 800 is a peristaltic or other type as needed, and the pump control signal 805 between the stimulator-detector 600 and the pump 800 may be wired or wireless.

Mathematical description of sensor-analyte binding: In order to work properly, the analyte binding site 110 of the sensor 100 should be analyte 215 specific and not become saturated in the analyte 215 concentration range of interest. Using first-order Michaelis-Menten binding dynamics to represent the analyte-sensor interaction

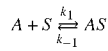

where A represents the free (unbound) analyte 215, S the free sensor 100, AS the analyte-sensor bound complex 210, $k_1$ the rate constant of the AS complex association, and $k_{-1}$ is that of the complex disassociation. The molar rate of AS formation, is given by $$\dot{AS}=k_1[A][S]-k_{-1}[AS]$$

where the notation [ ] represents molar concentration. This chemical reaction is fast compared to the changes in [A] or [S] or [AS], and the steady state condition describes its outcome as $$\dot{AS}\equiv 0$$

$$\therefore k_1[A][S]=k_{-1}[AS]$$

The dissociation constant, K, has units of concentration and may be determined experimentally as $$K\equiv\frac{k_{-1}}{k_1}$$
$$=\frac{[A]^*[S]^*}{[AS]^*}$$

where the * notation implies a measured value. Re-writing while using K:

$$[A][S]=K[AS] \quad (1)$$

$$\therefore [A]=K\frac{[AS]}{[S]}$$

In terms of the total sensor 100 concentration:

$$[S_{total}]=[S]+[AS]$$

$$\therefore [A]([S_{total}]-[AS])=K[AS] \quad (2)$$

In terms of the total analyte 215 concentration:

$$[A_{total}]=[A]+[AS]$$

$$\therefore ([A_{total}]-[AS])([S_{total}]-[AS])=K[AS] \quad (3)$$

After dividing both sides by $[S_{total}]^2$, this is written in terms of the fraction, $f_{Sbound}$, of bound sensor 210 as $$f_{Sbound}\equiv\frac{[AS]}{[S_{total}]} \quad (4)$$

$$\left(\frac{[A_{total}]}{[S_{total}]}-f_{Sbound}\right)(1-f_{Sbound})=\frac{Kf_{Sbound}}{[S_{total}]}$$

Re-writing:

$$f_{Sbound}^2-\left(1+\frac{[A_{total}]+K}{[S_{total}]}\right)f_{Sbound}+\frac{[A_{total}]}{[S_{total}]}=0$$

and solving this quadratic equation for $f_{Sbound}$:

$$f_{Sbound}=\frac{\left(1+\frac{[A_{total}]+K}{[S_{total}]}\right)-\sqrt{\left(1+\frac{[A_{total}]+K}{[S_{total}]}\right)^2-4\frac{[A_{total}]}{[S_{total}]}}}{2} \quad (5)$$

The bound fraction ranges from 0 to 1, and the free unbound fraction is given by $$f_{Sfree}=1-f_{Sbound} \quad (6)$$

Solving for the condition causing the bound fraction to have a value of ½:

$$\frac{1}{2}=\frac{\left(1+\frac{[A_{total@saturation/2}]+K}{[S_{total}]}\right)-\sqrt{\left(1+\frac{[A_{total@saturation/2}]+K}{[S_{total}]}\right)^2-4\frac{[A_{total@saturation/2}]}{[S_{total}]}}}{2} \quad (7)$$

$$\therefore K=[A_{total@saturation/2}]-\frac{[S_{total}]}{2}$$

$$\therefore [S_{total}]=2([A_{total@saturation/2}]-K) \quad (8)$$

Re-writing (4)

$$[A_{total}]=\left(\frac{K}{f_{Sfree}}+[S_{total}]\right)f_{Sbound} \quad (9)$$

Re-writing (2)

$$[A]=K\frac{f_{Sbound}}{f_{Sfree}} \quad (10)$$

Mathematical description of signaling: Say each mole of bound sensor 210 produces a quanta stimulus response signal 130 (quanta of fluorescence, light absorption or transmission, radio-frequency emission, etc), $\lambda_{quanta}$. If at time t=0 m(0) moles of sensor 100 are infused and an ensemble response signal 130, σ(0), is measured, then $$\sigma(0) = k_{measured\_space} m(0) \lambda_{quanta}$$

where $k_{measured\_space}$ represents the fraction of the whole body imaged 625 for the measurement. In terms of the concentration of bound sensor 210, a signal at any time t since the sensors 100 were administered is given by:

$$\sigma(t) = k_{measured\_space} m(t) \lambda_{quanta}$$

$$= k_{measured\_space} V_{distribution} [AS(t)] \lambda_{quanta} \quad (11)$$

where $V_{distribution}$ is the volume of distribution. If, for example, the signal is generated only when the sensor 100 is bound to analyte 215, in terms of the concentration of total sensors 100, $$\sigma(t) = k_{measured\_space} V_{distribution} f_{Sbound}(t) [S_{total}(t)] \lambda_{quanta} \quad (12)$$

As analyte 215 is added, σ(t) begins near zero and ranges up to an asymptotic value as the analyte binding sites 110 become saturated.

Calibrating to the subject: The value of $\lambda_{quanta}$ is known by the design of the sensor 100. If the value of product ($k_{measured\_space} V_{distribution}$) were also known, then from (12)

$$f_{Sbound}(t) = \frac{\sigma(t)}{(k_{measured\_space} V_{distribution}) \lambda_{quanta} [S_{total}(t)]}$$

$$f_{Sfree}(t) = 1 - f_{Sbound}(t)$$

and, from (9) and (10), $$[A_{total}(t)] = \left(\frac{K}{f_{Sfree}(t)} + [S_{total}(t)]\right) f_{Sbound}(t)$$

$$[A(t)] = K \frac{f_{Sbound}(t)}{f_{Sfree}(t)}$$

One method to determine the product value is by titrating analyte 215 into the subject until the stimulus response signal 130 reaches its asymptotic value while independently measuring the total analyte 215 concentration associated with the signal value. When the asymptotic value is achieved, the half-saturation analyte concentration is that measured at a signal level half of the asymptote. At this point $f_{Sbound} = ½$ and, from (8)

$$[S_{total}(0)] = 2([A_{total@saturation}/2] - K)$$

From (12):

$$\sigma_{saturation/2} = \frac{(k_{measured\_space} V_{distribution}) [S_{total}(0)] \lambda_{quanta}}{2}$$

$$\therefore (k_{measured\_space} V_{distribution}) = \frac{\sigma_{saturation/2}}{([A_{total@saturation/2}] - K) \lambda_{quanta}}$$

Having determined the pertinent parameters, and modeling the concentration of total sensors 100 as a decaying exponentially with the half-life of the transporter-eliminator 205, say albumin, the concentration of total sensors 100 at any time is given as $$[S_{total}(t)] = [S_{total}(0)] e^{kt} \quad (13)$$

where K is the known decay rate of the sensors 100. If bound to albumin, this is $$T_{albumin-halflife} = 20 \text{ days}$$

$$\kappa = \frac{1}{T_{albumin-halflife}} \ln\left(\frac{1}{2}\right)$$

$$= \frac{-0.0347}{\text{day}}$$

Figure 11:
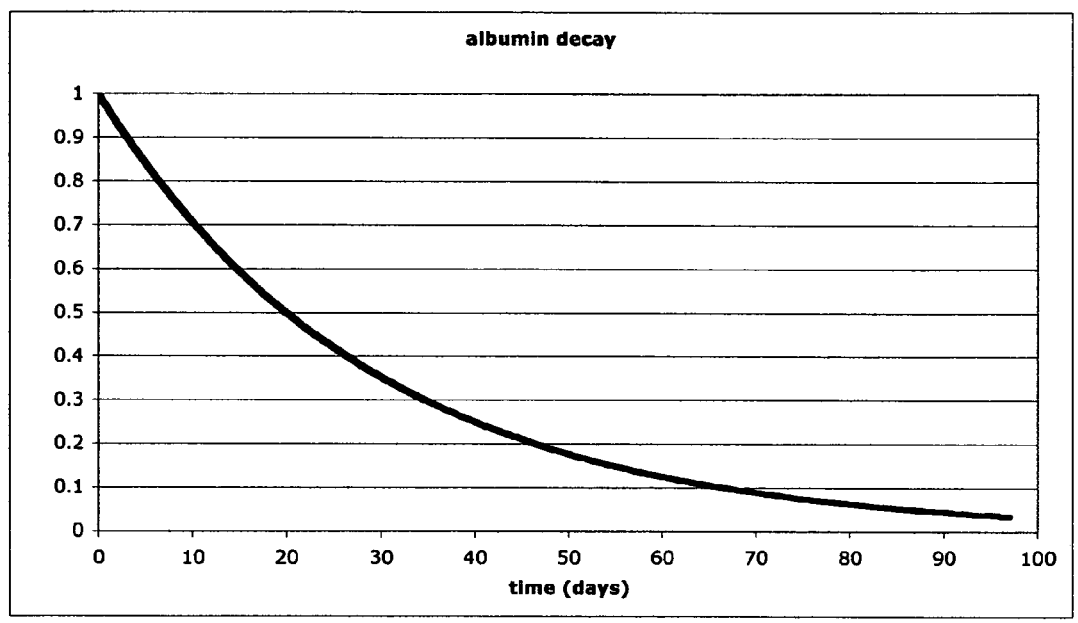
FIG. 11 is a graph of albumin half-life decay rate.

The decay of albumin is illustrated in FIG. 11. From (12):

$$f_{Sbound}(t) = \frac{\sigma(t)}{(k_{measured\_space} V_{distribution}) \lambda_{quanta} [S_{total}(t)]} \quad (14)$$

$$= \frac{\sigma(t)}{(k_{measured\_space} V_{distribution}) \lambda_{quanta} [S_{total}(0)] e^{\kappa t}}$$

$$f_{Sfree}(t) = 1 - f_{Sbound}(t) \quad (15)$$

From (9) the concentration of total analyte 215 is $$[A_{total}(t)] = \left(\frac{K}{f_{Sfree}(t)} + [S_{total}(t)]\right) f_{Sbound}(t) \quad (16)$$

$$= \left(\frac{K}{f_{Sfree}(t)} + [S_{total}(0)] e^{\kappa t}\right) f_{Sbound}(t)$$

and from (10) the concentration of unbound and physiologically active analyte 215 is $$[A(t)] = K \frac{f_{Sbound}(t)}{f_{Sfree}(t)} \quad (17)$$

As illustrated in the following example, these results provide a framework for designing the binding characteristics of the sensor.

Calibration also includes determination of normal background signal generation to compensate measurements made after sensors 100 are introduced.

Example of monitoring blood glucose: Consider a 70 kg diabetic subject. The human body contains a total of 4–6 gm/kg albumin, or around 350 gm for the subject. As albumin has a molecular weight of 66,200 gm/mole, there are around 5.28 mmoles with 2.22 mmole intravascular (42%) and 3.07 mmole extravascular (58%). Targeting one out of twenty albumin molecules to carry a sensor 100, the sensor administration 510 contains m(0)=5.28/20=0.264 mmoles Using blood volume as $V_{distribution}$, $[S_{total}(0)] = m(0) / V_{distribution} = 0.00467$ mmole/100 ml Blood glucose exists primarily in an unbound state and is freely distributed in blood 505. Normal fasting levels in venous blood are 60–80 mg/100 ml and 75–110 mg/100 ml in arterial blood and it has a molecular weight of 120.1 gm/mole. Choose the sensor 100 to have a glucose half-saturation response of $[G_{total@saturation/2}] = 100$ mg/100 ml=0.833 mmole/100 ml where [G] is the concentration of the glucose analyte 215 in blood. Under these conditions the glucose binding site 110 should be designed using (7) such that $$K=0.833-0.00467/2=0.830 \text{ mmole/100 ml}=8300 \text{ μmole/liter}=8300 \text{ μM}$$

Protein receptors for reversibly binding analytes are generally modified versions of those found in nature. The modification process includes inserting modifiers within the protein matrix to alter the dissociation constant, and it is generally much easier to increase the constant (weaken the bond) than to decrease it. Using GGBP from *Escherichia coli* as the natural receptor, having dissociation constant around 0.8 μM, for this example the bond must be weakened to increase K.

Figure 12:
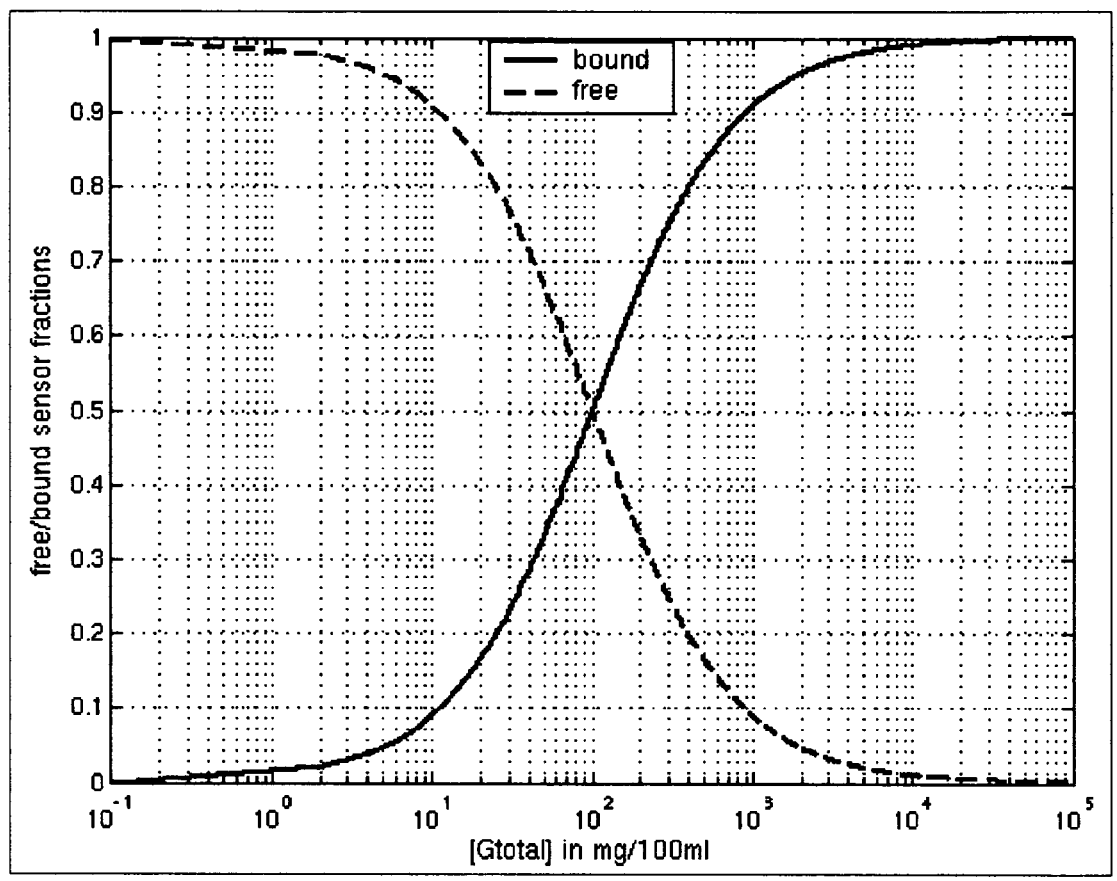
FIG. 12 is a semi-logarithmic graph illustrating sensor bound and free fractions vs. total blood glucose concentration.

The bound and free fractions of sensor receptors 110 as a function of total blood glucose concentration adhere to the curve shown in FIG. 12. This curve is determined by converting $[G_{total}]$ from mass concentration into molar concentration using the glucose molecular weight, and determining $f_{Sbound}$ and $f_{Sfree}$ using (5) and (6).

Figure 13:
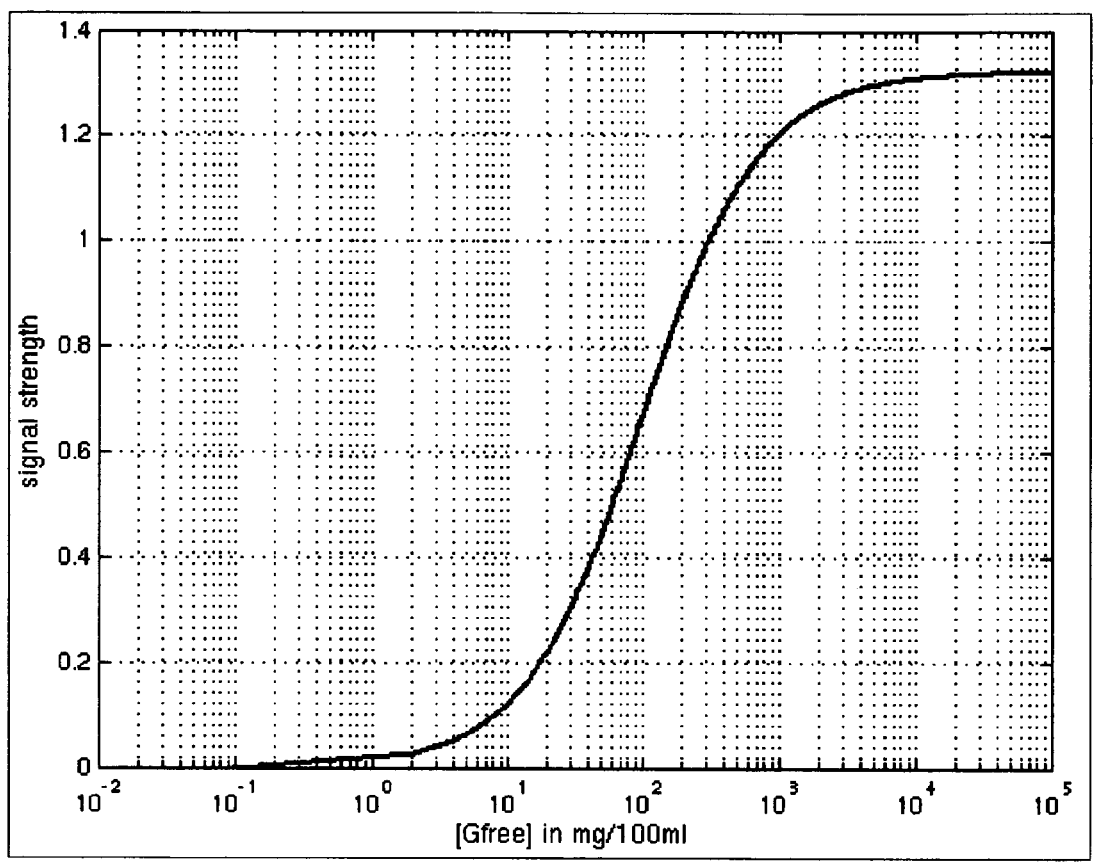
FIG. 13 is a semi-logarithmic graph illustrating sensor signal strength vs. unbound blood glucose concentration.
Figure 14:
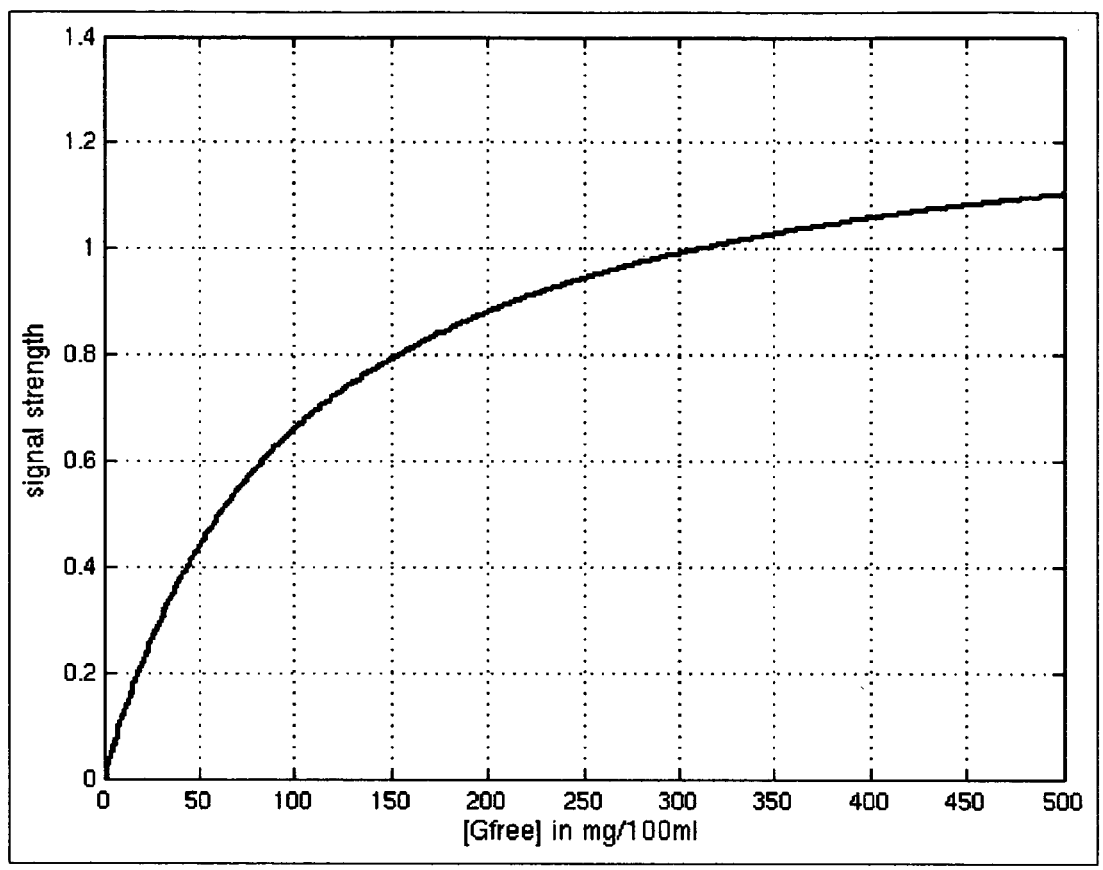
FIG. 14 is a linear graph illustrating sensor signal strength vs. unbound blood glucose concentration in normal operating range.

Using a normalized signaling index of $$\lambda_{quanta} = 100 \text{ units/mmole}$$

and $$k_{measured\_space} = 0.05 \text{ of the total body (roughly a forearm)}$$

the signal 130 strength, as a function of metabolically active free glucose concentration, adheres to the curve shown in FIG. 13. This graph is determined from the data of FIG. 12 by using (10) to calculate the free glucose concentration and (12) to calculate the signal strength. A linear plot of these results restricted to the normal glucose operating point is shown in FIG. 14.

Figure 15:
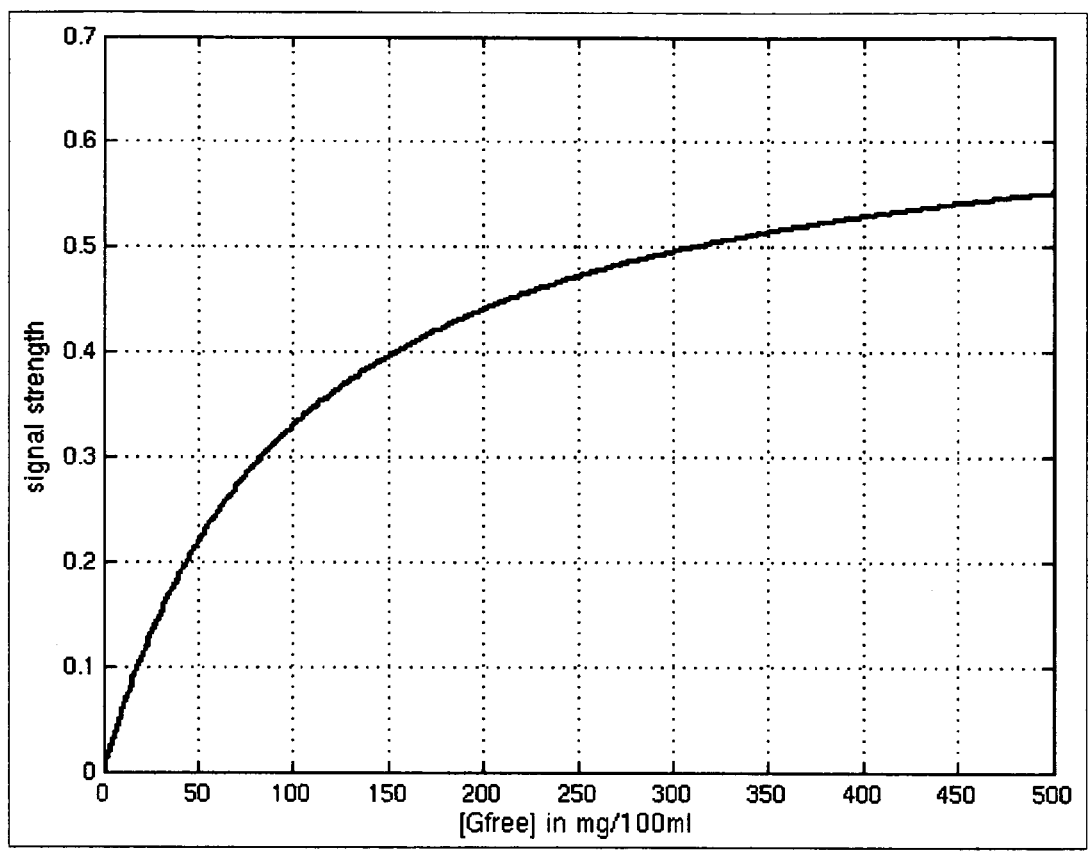
FIG. 15 is a linear graph illustrating sensor signal strength vs. unbound blood glucose concentration after 20 days.

After 20 days, the half-life of albumin, the number of sensors 100 is predictably halved but, as shown in FIG. 15, the shape of the signal vs. free glucose concentration curve is unchanged. Because the decay of sensor receptor sites 110 is known and compensated for in (13)–(17), the ability to measure [G] is unaffected although the signal-to-noise ratio of the measurements is halved.

Alternative calibration: Glucose should not exceed 200 mg/100 ml or it is excreted into urine. Given this limit, determination of the saturation level may not be feasible and calibration based on the half-saturation value not workable or even dangerous to health. Rather, the mathematical curve representing this response is adjusted to fit the observed response by curve fitting the following coupled equations to minimize the square error:

from (11):

$$[AS(t_n)] = \frac{\sigma*(t_n)}{k_{measured\_space} V_{distribution} \lambda_{quanta}}$$

from (13):

$$[S_{total}a(t_n)] = [S_{total}a(0)] e^{kt_n} \text{ from (3)}:$$

$$\text{error}(t_n) = ([A^*_{total}(t_n)] - [AS(t_n)])([S_{total}(t_n)] - [AS(t_n)]) - K[AS(t_n)]$$

$$\text{square\_error} = \sum_{n=1}^{N} \text{error}^2(t_n)$$

Here the * annotated terms are measured data. Curve fitting is applied to data taken over a limited titration range from, say, very low analyte up to high normal range.

Taking first the simpler case where the data is taken quickly in contrast to the sensor decay rate, these equations are combined such that the error is written linearly in terms of three β constants that are to be determined by curve fitting the error to the σ*(t) and [A*$_{total}$(t)] data $$\text{error}(t_n) = \{\sigma*(t_n)\}^2 + \beta_1 \sigma*(t_n) + \beta_2 [A_{total}*(t_n)]\sigma*(t_n) + \beta_3 [A_{total}*(t_n)]$$

where $$\beta_1 = -([S_{total}(0)]+K) k_{measured\_space} V_{distribution} \lambda_{quanta}$$

$$\beta_2 = -k_{measured\_space} V_{distribution} \lambda_{quanta}$$

$$\beta_3 = (k_{measured\_space} V_{distribution} \lambda_{quanta})^2 [S_{total}(0)]$$

Because each of the β constants uniquely determines the shape of the error curve, they are identifiable and can be estimated from the data. The error is written linearly in matrix-vector terminology in terms of the β constants as $$\text{error}(t_n) = \{\sigma*(t_n)\}^2 + \underline{v}(t_n)\underline{b}$$

$$\underline{v} = [\sigma*(t_n)[A^*_{total}(t_n)]\sigma*(t_n)[A^*_{total}(t_n)]]$$

$$\underline{b} = \begin{bmatrix} \beta_1 \\ \beta_2 \\ \beta_3 \end{bmatrix}$$

Since the minimum least square error occurs when the derivative of square_error with respect to the vector b is zero, $$\text{square\_error} = \sum_{n=1}^{N} [\{\sigma*(t_n)\}^2 + \underline{v}(t_n)\underline{b}]^2$$

$$\frac{d}{d\underline{b}} \text{square\_error} = 2 \sum_{n=1}^{N} [\underline{v}^T(t_n)\{\sigma*(t_n)\}^2 + \underline{v}^T(t_n)\underline{v}(t_n)\underline{b}] = \underline{0}$$

$$\therefore \sum_{n=1}^{N} \{\underline{v}^T(t_n)\underline{v}(t_n)\}\underline{b} = -\sum_{n=1}^{N} \{\underline{v}^T(t_n)[\sigma*(t_n)]^2\}$$

and is solved exactly without iteration as $$\underline{b} = -\left(\sum_{n=1}^{N} \underline{v}(t_n)^T \underline{v}(t_n)\right)^{-1} \sum_{n=1}^{N} [\sigma*(t_n)]^2 \underline{v}^T(t_n)$$

Given the values of the β constants, K, $[S_{total}(0)]$ and the product $k_{measured\_space} V_{distribution} \lambda_{quanta}$ are determined as $$k_{measured\_space} V_{distribution} \lambda_{quanta} = -\beta_2$$

$$[S_{total}(0)] = \frac{\beta_3}{\beta_2^2}$$

$$K = \frac{\beta_1 \beta_2 - \beta_3}{\beta_2^2}$$

from which (13–17) are completely determined.

If the sensor decay rate must be accounted for, the terms are no longer simple constants but are given by $$\beta_1 = -([S_{total}(0)]e^{kt_n}+K)k_{measured\_space}V_{distribution}\lambda_{quanta}$$

$$\beta_2 = -k_{measured\_space}V_{distribution}\lambda_{quanta}$$

$$\beta_3 = (k_{measured\_space}V_{distribution}\lambda_{quanta})^2[S_{total}(0)]e^{kt_n}$$

and K, $[S_{total}(0)]$ and the product $k_{measured\_space}V_{distribution}\lambda_{quanta}$ are curve fit directly without first estimating the β values. Any number of nonlinear schemes are used such as gradient descent, Newton-Raphson, etc.

An alternate approach where both binding states are reported: The sensor signaling site 105 is alternately designed to provide two separable indications: bound and unbound to analyte 215. This is a signaling site 105 that responds 130 to the same stimulus 125 in two different and detectable manners depending on the analyte binding site status, or to one of two different stimuli 125 depending on the status.

In the case of fluorescence, an example is a signaling site 105 that fluoresces and responds 130 at one wavelength with a given stimulus 125 when the binding site 110 is bound to analyte 215, and responds 130 with another wavelength to the same stimulus 125 when unbound. The stimulator-detector 600 queries both the bound sensors and the unbound sensors simultaneously and in parallel, and detector 620 distinguishes their separable responses 130. In another example, the signaling site 105 responds 130 to a stimulus 125 of one wavelength when bound to analyte 215 and to a stimulus 125 of a second wavelength when unbound, and the stimulator-detector 600 serially queries the bound and unbound sensors with one and then the other stimulus.

In the case of nuclear magnetic resonance, an example is a signaling site 105 that resonates and responds 130 with one radio frequency stimulus 125 when the binding site 110 is bound to analyte 215, and to another stimulus when unbound, or has different responses 130 (e.g. relaxation time constant) to the same stimulus 125. There are obvious parallel and serial query approaches.

If $\sigma_{bound}$ is a measured signal representing the response 130 to being bound and σbound the response to a being unbound to analyte 215, then from (11)

$$\sigma_{bound} = k_{measured\_space}V_{distribution}[AS]\lambda_{quanta@bound}$$

$$\therefore [AS] = \frac{\sigma_{bound}}{k_{measured\_space}V_{distribution}\lambda_{quanta@bound}}$$

$$\sigma_{unbound} = k_{measured\_space}V_{distribution}[S]\lambda_{quanta@unbound}$$

$$\therefore [S] = \frac{\sigma_{unbound}}{k_{measured\_space}V_{distribution}\lambda_{quanta@unbound}}$$

From (1) the concentration of unbound and physiologically active analyte 215 is $$[A(t)] = K\frac{\lambda_{quanta@unbound}}{\lambda_{quanta@bound}}\frac{\sigma_{bound(t)}}{\sigma_{unbound(t)}}$$

It is not necessary to know $k_{measured\_space}$ nor $V_{distribution}$ nor the decay time constant κ, and subject calibration and a known transporter-eliminator 205 decay rate are not required.

A measure of the total number of binding sites 110 remaining is given by the $$numberBindingSites \propto \frac{\sigma_{unbound}}{\lambda_{quanta@unbound}} + \frac{\sigma_{bound}}{\lambda_{quanta@bound}}$$

where ∝ indicates proportionality. This is used to determine the decay of sensors 100 and when more should be introduced.

Alternative Embodiments. While several illustrative embodiments of the invention have been shown and described, numerous variations and alternate embodiments will occur to those skilled in the art. For example, the analyte measurement may be other than concentration, such as merely determining existence of analytes in the body fluids; the external noninvasive stimulator-detector device is embedded within the subject; the analyte binding involves intermediate reactions where higher order Michaelis-Menten reactions are involved; the interaction between the analyte binding site and the signaling site is other than conformational changes. Analyte binding site and transporter-eliminator binding site can be synthetic as well as naturally-occurring substances. Such variations and alternate embodiments, as well as others, are contemplated and can be made without departing from the spirit and scope of the invention as defined in the appended claims.

What is claimed is:

1. An apparatus for measuring an analyte in the body fluids of a subject comprising:
    a plurality of sensors that undergo a physical or chemical or electrical or optical change when bound to an analyte, each sensor responsive to said change and to at least one stimulating signal and responsively generating at least one reporting signal, each sensor adapted to bind to a body fluid transporter for transport through the subject body fluids and for elimination where the elimination rate of the transporter is known;
    a stimulator generating the at least one stimulating signal;
    at least one detector responsive to said plurality of reporting signals and responsively generating at least one detector signal; and
    a processor configured to determine an analyte measurement in response to the at least one detector signal and the known transporter elimination rate,
    whereby, said plurality of sensors is transported through the body fluids bound to a plurality of said transporters.

2. The apparatus according to claim 1, wherein each of said sensors comprises:
    a reversible analyte binding site;
    a signaling site responsive to the bound and unbound status of the analyte binding site and to said at least one stimulating signal and generating said at least one reporting signal accordingly; and
    a binding site adapted to bind to said transporter.

3. The apparatus according to claim 2 wherein the binding characteristics of said analyte binding site are known and said analyte measurement is further responsive to the known binding characteristics.

4. The apparatus according to claim 1, wherein said at least one stimulating signal is taken from the electromagnetic spectrum.

5. The apparatus according to claim 1, wherein at least one stimulating signal is magnetic.

6. The apparatus according to claim 1, wherein said at least one reporting signal is fluorescence.

7. The apparatus according to claim 1, wherein at least one reporting signal is within the radio frequency spectrum.

8. The apparatus according to claim 1, wherein said body fluid transporter comprises an endogenous blood component.

9. The apparatus according to claim 1, wherein said at least one stimulating signal is generated by a nuclear magnetic resonance imaging device, and said at least one detector and said processor are components of the nuclear magnetic resonance imaging device.

10. The apparatus according to claim 9, wherein said measurement comprises the location of said at least one reporting signal within the subject.

11. A method for measuring an analyte in the body fluids of a subject comprising the steps of:
   administering a plurality of sensors into the subject body fluids, each of said sensors comprising:
      a reversible analyte binding site;
      a signaling site responsive to the bound and unbound status of the analyte binding site and to at least one external stimulating signal and responsively generating at least one reporting signal; and
      a binding site to a body fluid transporter, said transporter providing sensor transport through the body fluids and elimination where the elimination rate of said transporter is known;
   providing the at least one stimulating signal;
   generating at least one detector signal in response to said reporting signals;
   determining the analyte measurement in response to the at least one detector signal and the known transporter elimination rate; and
   outputting the analyte measurement.

12. The method according to claim 11, wherein the binding characteristics of said analyte binding site are known and said analyte measurement is further responsive to the known binding characteristics.

13. The method according to claim 11, wherein said body fluid transporter comprises an endogenous blood component.

14. The method according to claim 11 including the step of binding said transporter to said sensor prior to sensor administration into said body fluids.

* * * * *